US00PP17224P3

(12) United States Plant Patent

Giumarra et al.

(10) Patent No.: US PP17,224 P3

(45) Date of Patent: Nov. 21, 2006

(54) GRAPE PLANT NAMED 'ARRATHREE'

(50) Latin Name: ***Vitis* sp.**
Varietal Denomination: Arrathree

(75) Inventors: Salvador Giumarra, Edison, CA (US); Shachar Karniel, Edison, CA (US)

(73) Assignee: Agricultural Research & Development, LLC, Edison, CA (US)

( * ) Notice: Subject to any disclaimer, the term of this patent is extended or adjusted under 35 U.S.C. 154(b) by 0 days.

(21) Appl. No.: 11/028,715

(22) Filed: Jan. 3, 2005

(65) Prior Publication Data

US 2006/0150288 P1 Jul. 6, 2006

(51) Int. Cl.
*A01H 5/00* (2006.01)

(52) U.S. Cl. ..... Plt./205

(58) Field of Classification Search ..... Plt./205
See application file for complete search history.

*Primary Examiner*—Kent Bell
*Assistant Examiner*—June Hwu
(74) *Attorney, Agent, or Firm*—Christie, Parker & Hale, LLP

(57) ABSTRACT

A new and distinct variety of Grapevine, designated 'Arrathree', characterized by strong vegetation, on own root and when grafted, high yield and large bunches, fire bright red berry color with very uniform coverage and color that does not get darker as ripening goes on, somewhat tight bunches, and very uniform berries, meaty with no water berries, that do not stutter or crack.

2 Drawing Sheets

Botanical classification/cultivar denomination: *Vitis* sp. cultivar Arrathree.

BACKGROUND OF THE INVENTION

The present invention relates to a new and distinct variety of Grapevine, botanically known as *Vitis* sp., and hereinafter referred to by the name 'Arrathree'.

SUMMARY OF THE INVENTION

'Arrathree' was bred by embryo rescue from the cross S.R. 43/25×FL R47/63-229. It has been asexually reproduced in Salinas, Calif., by tissue culture, emasculating seedless mother pollened with seedless father, and the seed trace rescued in tissue culture process, and by grafting. Observations made on 'Arrathree' since May 1997 have shown that the unique features of this new Grapevine are stable and reproduced true to type in successive generations.

The new variety differs from other cultivars known to the inventor, including its parents, in the following traits, which have been repeatedly observed and are determined to be the unique and stable characteristics of 'Arrathree':

1. Strong vegetation variety, on own root and when grafted;
2. Produces high yield and large bunches;
3. Berry color is fire bright red, very uniform coverage, color does not get darker as ripening goes on;
4. Bunches are somewhat tight;
5. Doesn't shatter or crack, berries are very uniform, meaty with no water berries;
6. Midseason variety, ripening in the third week of July.

These characteristics in combination distinguish 'Arrathree' as a new and distinct Grapevine cultivar. All observations were made from four year old specimens grown in Bakersfield, Calif., from April to September 2003.

BRIEF DESCRIPTION OF ILLUSTRATIONS

The accompanying photographic illustrations show typical specimens of four year old specimens of the new variety, in color as nearly true as it is reasonably possible to make in a color illustration of this character. Colors in the photograph may differ from the color values cited in the detailed botanical description below, which accurately describes the colors of the new Grapevine.

Figure 1:
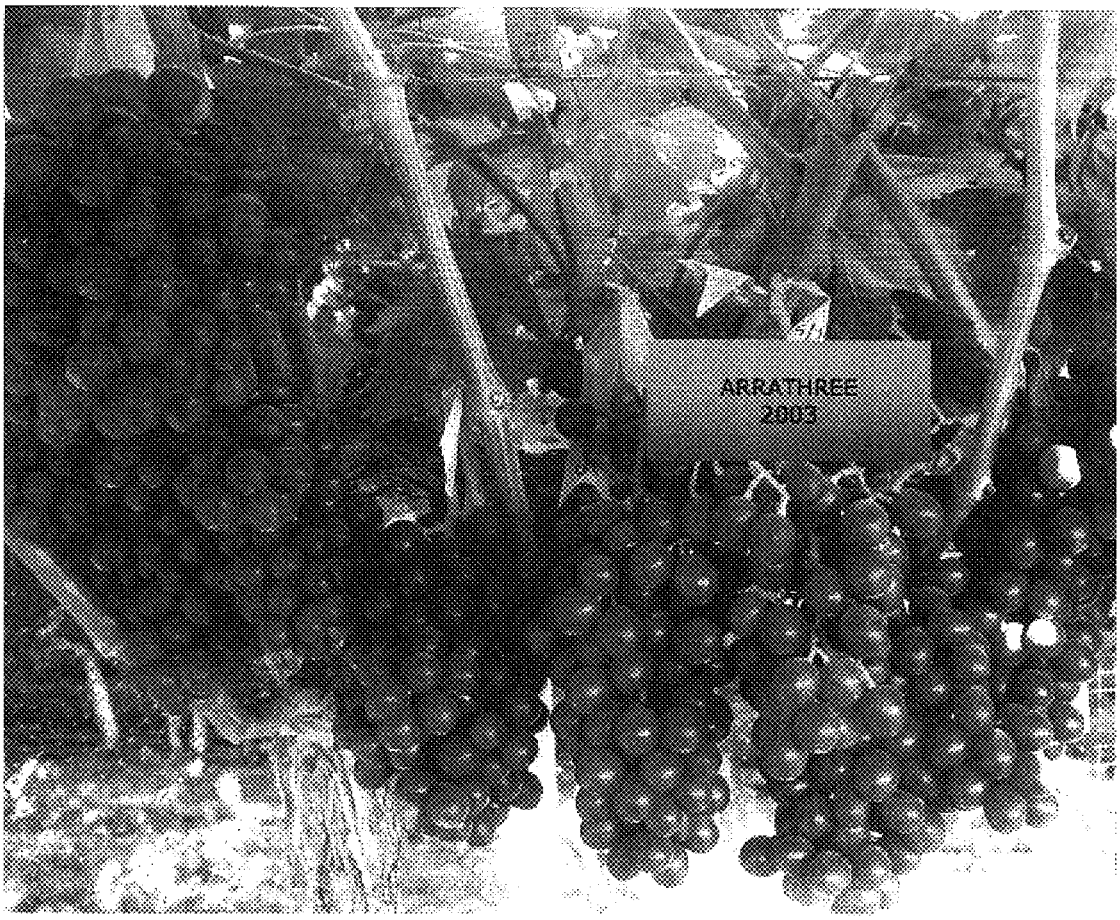

FIG. 1 comprises leaves, stems and grapes of 'Arrathree'.

Figure 2:
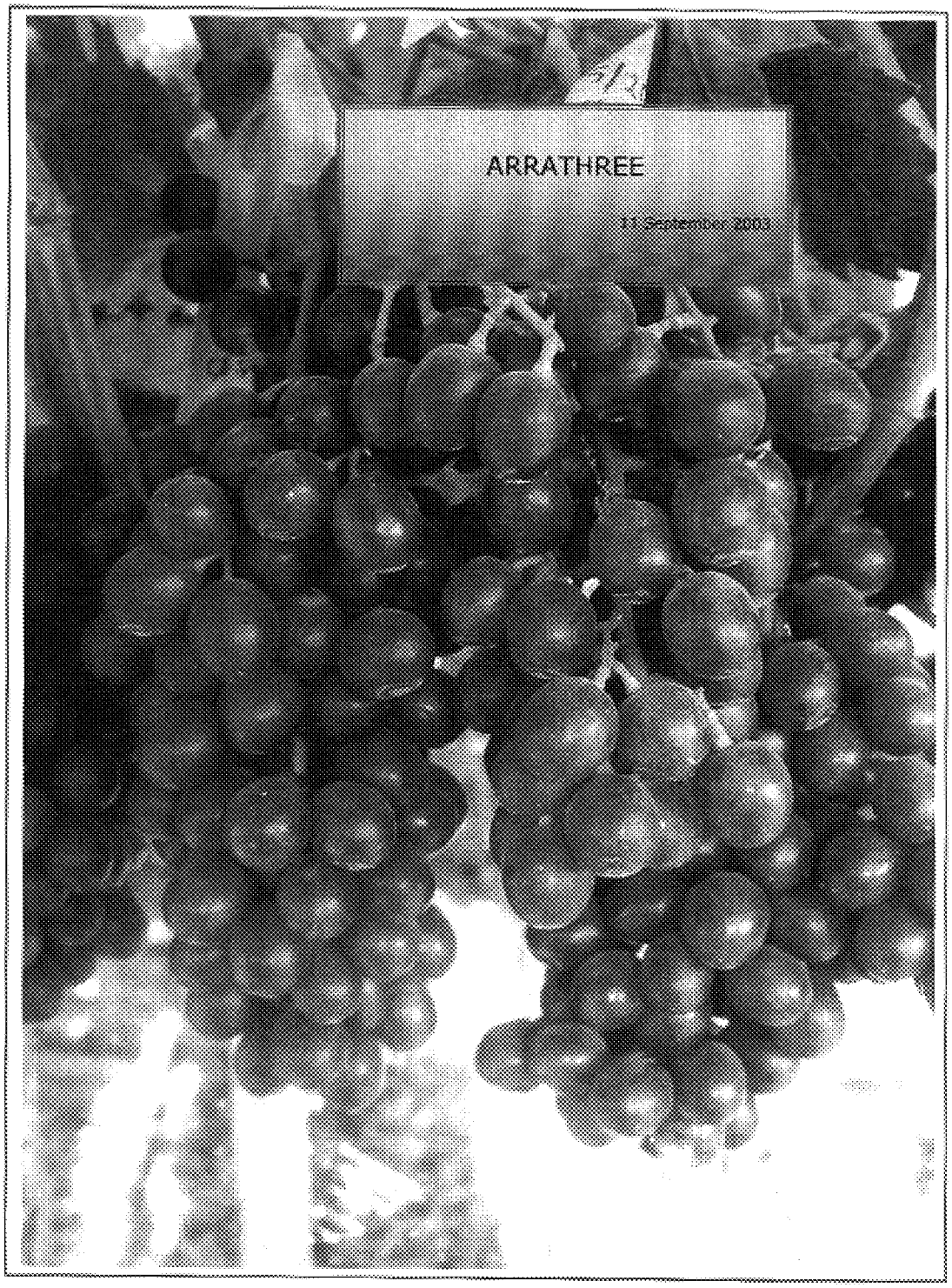

FIG. 2 comprises a close-up of bunches of 'Arrathree'.

DESCRIPTION OF THE NEW VARIETY

Referring now specifically to the new and distinct variety of Grapevine, the following is a detailed description of 'Arrathree' with color description where indicated by reference to The Royal Horticultural Society Colour Chart, except where common terms of color definition are employed.

The new variety of Grapevine as herein described may vary in slight detail due to climatic, soil and cultural conditions under which the variety may be grown, the present description being of four year old specimens of the variety as grown from its own root at Bakersfield, Calif., between April and September of 2003.

Plant characteristic:

*Form.*—Upright with an extremely long and large canopy.

*Growth.*—High, vigorous growth, with large canes and wide trunk.

Vegetative characteristics:

*Trunk.*—Size — medium developed for age, ranges from 2.0 to 2⅜ inches measured within a few inches from the base of the trunk. Surface texture — rough with a fibrous, shaggy exterior. Color — light maple brown (brown group 200/C mixed with large strips of Greyed-orange 177/B).

*Young shoot.*—Form of tip — Fully open. Anthocyanin coloration of tip — Absent. Density of prostrate hairs on tip — Very sparse. Density of erect hairs on tip — Very sparse. Color of dorsal side of internode (Well illuminated) — Completely green (Yellow green group near 144A). Color of ventral side of internode (Without direct sunlight) — completely green (Yellow green group near 144A).

*Mature shoot.*—Attitude (habit) — Erect. Color of dorsal side of internode (Well illuminated) — Greyed orange group near 175B with reddish stripes (Greyed orange group near 166C). Color of ventral side of internode (Without direct sunlight) — Greyed Orange Group near 175B. Color of dorsal side of node (Well illuminated) — Green and red striped (Yellow green group near 144A). Color ventral side of node (without direct sunlight) — completely green, (Yellow green group near 144A). Density of erect hairs on node — Very sparse. Erect hairs on internode — Present. Density of prostrate hairs on node — Very sparse. Density of prostrate hairs on internode — Very sparse. Number of consecutive tendrils — Three or more. Length of tendrils — average length 3½ to 4½ inches.

*Young leaf.*—Color of upper surface (recorded on the first 4 distal unfolded leaves — Green (Yellow green group near 146C). Density of prostrate hairs between veins (Recorded on the lower surface of the 4$^{th}$ distal unfolded leaf) — Very sparse. Density of erect hairs between veins (recorded on the lower surface of the 4$^{th}$ distal unfolded leaf) — Very sparse. Density of prostrate hairs on main veins (recorded on the lower surface of the 4$^{th}$ distal leaf) — Very sparse. Density of erect hairs on main veins (recorded on the lower surface of the 4$^{th}$ distal leaf) — Very sparse.

*Mature leaf.*—Size of blade (Recorded on mature leaves above the cluster within the medium third of shoot) — Large, about 8 inches by 5¾ inches. Shape of blade — Circular. Size of leaf: length about 8 inches, width about 5¾ inches. Top color — Green group near 137A. Bottom color — Green group near 137D. Petiole color — Yellow green group near 144C with Greyed orange group near 176C. Anthocyanin coloration on main veins on upper side of blade (Recorded on leaves above the cluster at the medium third of shoot) — Absent. Profile (cross-section at the middle of the leaf blade) — V-shaped. Blistering of blade upper surface — Absent. Shape of teeth (Recorded on the lateral lobe) — Both sides straight (rectilinear). Length of teeth: Medium. Ratio length/width of teeth — Medium. General shape of petiole sinus (Degree of the opening of the petiole sinus) — Half open. Tooth of petiole sinus — Absent. Petiole sinus limited by veins — Absent. Shape of upper lateral sinus (Degree of the opening of the upper lateral sinus). A sinus results from a clear interruption of teeth on the leaf margin. The upper lateral sinus is situated between the middle vein and next lateral main vein — open. Depth of upper lateral sinus — Deep, about 1 inch. Density of prostrate hairs between veins (recorded on the lower side of blade) — Very sparse. Density of erect hairs between veins (Recorded on the lower side of blade) — Dense. Density of prostrate hairs on main veins (Recorded on the lower side of blade) — Very sparse. Density of erect hairs on main veins (Recorded on the lower side of blade) — Very sparse. Density of prostrate hairs on main veins (Recorded on the upper surface of the blade) — Present. Length petiole compared to middle vein — Equal average length ⅛ inch.

*Woody shoot.*—Surface — Ribbed. Main color — Greyed orange group near 175B with yellowish brown stripes (Greyed orange group near 166C).

Inflorescence and fruit:

*Inflorescence.*—Sex of flower — Male and Female fully developed.

*Flower.*—Color of pedicel — Light yellow/green (Yellow green group near 149D). Length of pedicel — ⅛ inch. Color of stamen — Yellow-green group near 148B. Length of stamen — ⅛ inch.

*Bunch.*—Size (without peduncle) — Large, length about 8¾ inches, width about 4½ inches. Density — Medium (densely distributed berries, pedicles not visible) Length of peduncle — average length ⅛ inch. Shape — conical. Number of berries — approximately 175 to 225 berries per bunch. Average weight — 1½ to 2.0 pound on untreated bunches. Color of peduncle — light yellow green (Yellow green near group 144D).

*Berry.*—Size — Medium 13⁄16", Berry weight about 4.7 g (+ Gibb), and 4.7 g (untreated). Shape — Obtuse-ovate. Presence of seed — Seed about 0.5×0.25 mm, berry width about 13⁄16 inch. Skin color (without bloom) light-dependent, recorded on berries which are exposed directly to sun — Red (Greyed purple group near 187B). Skin bloom — weak. Skin texture — none bloom, smooth, having slightly bistering, medium thick skin. Weight — 10 berries, about 47 g. Firmness of flesh (Weight necessary for cracking the berries) — Medium. Color of flesh — Red (Greyed purple group near 187B). Juiciness of flesh — meaty and juicy. Tenacity of flesh — meaty solid flesh. Particular flavor — None. Ease of detachment from pedicel — Difficult; brush length 3⁄16 inches.

*Seed.*—Length — Short. 100-seed weight — Very low. Transversal ridges on side — Present.

Plant descriptors: All information below based on growing the variety in the Southern part of California.

*Time of bud burst (only varieties for fruit production).*—Early flowering, in the last week of April.

*Inflorescence (number of inflorescence per shoot).*—One to two per shoot.

*Time of berry ripening (veraison).*—Second week of July.

*Bunch length (without peduncle).*—Naturally long bunches, from about 6½" to about 8½" in length.

*Berry thickness of skin (thickness of epidermis plus hypodermis).*—Thin, about 100 μm.

*Market use information.*—Shipping quality of the fruit is very good both in storage and transportation. The fruit also has an excellent keeping quality, including excellent shelf life, and attractive appearance on shelf for extend periods.

*Resistance/susceptibility to disease and pest.*—No difference from other *Vitis vinifera* varieties.

Comparison to Flame seedless: Flame seedless is the most popular red grape in the USA. It is early, crunchy and pleasant to eat.

Flame seedless is different from the new variety by the following:

'Arrathree' ripening time is three weeks later than Flame seedless;

'Arrathree' has a naturally larger berry than Flame seedless, Flame berry size is not commercially viable without applying growth regulators for increased berry size;

'Arrathree' does not crack at all while one of the major growing problems of Flame seedless is the non elastic skin which often cracks and causes rot; and 'Arrathree' has a natural bright red color fully covered from early stages of ripening, while in Flame seedless it is necessary to apply "Ethapon" growth regulator to enhance color when grown under the same conditions.

We claim:

1. A new and distinct variety of grapevine, botanically known as *Vitis* sp., identified as 'Arrathree', substantially as shown and described herein.

* * * * *